(12) United States Patent
Gardeski et al.

(10) Patent No.: US 6,544,247 B1
(45) Date of Patent: Apr. 8, 2003

(54) INTRODUCER SYSTEM

(75) Inventors: Kenneth C. Gardeski, Plymouth, MN (US); John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 128 days.

(21) Appl. No.: 09/656,721

(22) Filed: Sep. 7, 2000

Related U.S. Application Data

(62) Division of application No. 09/116,628, filed on Jul. 16, 1998, now Pat. No. 6,159,198.

(51) Int. Cl.$^7$ ............................................. A61M 31/00
(52) U.S. Cl. ................. 604/510; 604/164.05; 604/500; 604/523; 604/161; 604/167.01; 128/898
(58) Field of Search ................................. 604/104, 158, 604/160, 161, 164.01, 164.02–164.05, 167.01, 523, 500, 510, 506, 533, 537, 264, 164.1, 170.01–170.03, 167.06; 606/167

(56) References Cited

U.S. PATENT DOCUMENTS

| | | | |
|---|---|---|---|
| 4,473,067 A | | 9/1984 | Schiff |
| 4,772,266 A | * | 9/1988 | Groshong .................... 604/160 |
| 4,874,374 A | * | 10/1989 | Kousai et al. .......... 604/164.05 |
| 4,997,424 A | | 3/1991 | Little |
| 5,000,745 A | * | 3/1991 | Guest et al. ............. 251/149.1 |
| 5,125,904 A | | 6/1992 | Lee |
| 5,127,626 A | * | 7/1992 | Hilal et al. ............... 251/149.1 |
| 5,147,336 A | * | 9/1992 | Wendell et al. ............. 600/486 |
| 5,167,634 A | * | 12/1992 | Corrigan et al. ............ 604/160 |
| 5,188,605 A | * | 2/1993 | Sleep .......................... 604/158 |
| 5,221,263 A | * | 6/1993 | Sinko et al. ................ 604/161 |
| 5,250,033 A | | 10/1993 | Evans et al. |
| 5,267,982 A | | 12/1993 | Sylvanowicz |
| 5,269,764 A | * | 12/1993 | Vetter et al. ............. 251/149.1 |
| 5,334,157 A | * | 8/1994 | Klein et al. ................. 604/160 |
| 5,397,311 A | * | 3/1995 | Walker et al. .............. 604/160 |
| 5,409,469 A | | 4/1995 | Schaerf |
| 5,509,910 A | | 4/1996 | Lunn |
| 5,545,149 A | | 8/1996 | Brin et al. |
| 5,571,161 A | | 11/1996 | Starksen |
| 5,599,328 A | * | 2/1997 | Stevens ...................... 285/276 |
| 5,624,617 A | | 4/1997 | Sorabella et al. |
| 5,669,881 A | | 9/1997 | Dunshee |
| 5,766,203 A | * | 6/1998 | Imran et al. .......... 604/103.05 |
| 5,911,710 A | * | 6/1999 | Barry et al. ........... 604/167.04 |
| 5,951,518 A | * | 9/1999 | Licata et al. ................ 604/161 |
| 6,027,480 A | * | 2/2000 | Davis et al. ........... 604/164.05 |
| 6,080,141 A | * | 6/2000 | Castro et al. .......... 604/164.01 |
| 6,083,207 A | * | 7/2000 | Heck ........................... 604/160 |
| 6,228,052 B1 | * | 5/2001 | Pohndorf .................... 604/104 |
| 6,379,372 B1 | * | 4/2002 | Dehdashtian et al. .... 604/96.01 |

* cited by examiner

*Primary Examiner*—Brian L. Casler
*Assistant Examiner*—Cris L. Rodriguez
(74) *Attorney, Agent, or Firm*—Girma Wolde-Michael; Michael C. Soldner

(57) ABSTRACT

An introducer system for introducing a lead or catheter and a method of use. The introducer system includes an elongated introducer sheath which has a luer hub mounted to its proximal end through which a lead or catheter is introduced and a slitter for slitting the luer hub and the introducer sheath. The slittable luer hub takes the form of a conical or cylindrical member carrying a laterally extending tab adapted to engage internal threading on a female luer lock fitting and has a slittable portion angularly displaced from the tab. The slitter includes a blade, a handle carrying the blade, a mechanism for engaging the lead or catheter in the vicinity of the blade and a mechanism for engaging the lead or catheter proximal to the blade, configured such that the lead or catheter body when engaged by the slitter is angled proximal to the blade of the slitter.

5 Claims, 9 Drawing Sheets

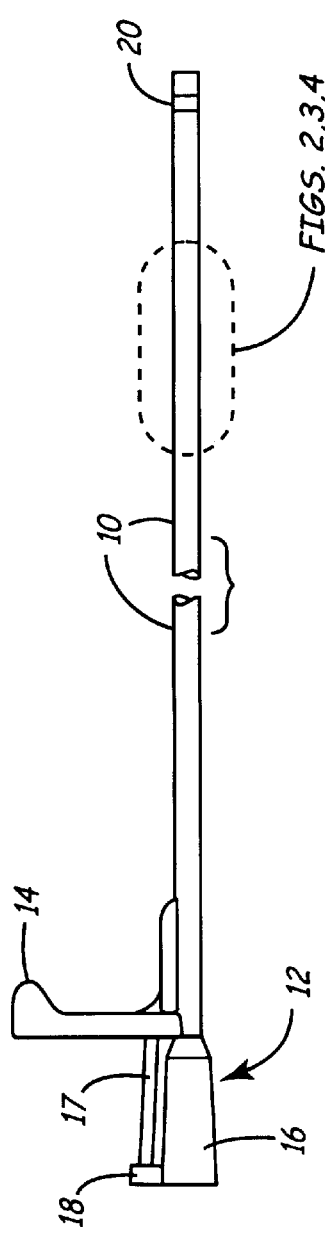
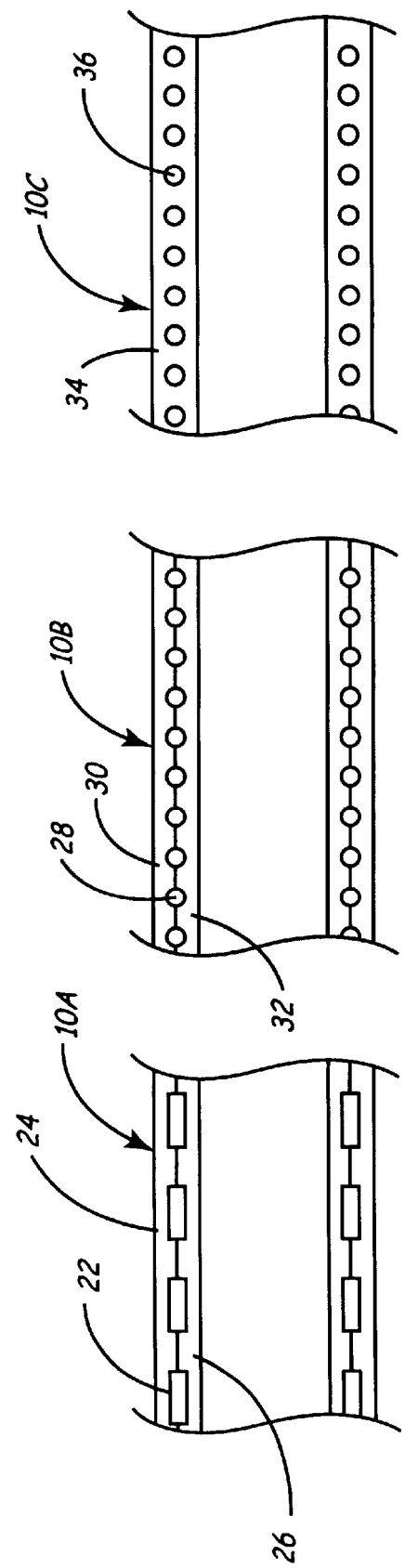

INTRODUCER SYSTEM

This application is a divisional of application number 09/116,628 filed Jul. 16, 1998, now U.S. Pat. No. 6,159,198.

BACKGROUND OF THE INVENTION

The present invention relates generally to indwelling catheters and electrode leads and more particularly to introducer systems for introducing catheters and electrode leads into a desired portion of a patient's body.

Catheters and leads are typically placed in a desired location in a patient's body, particularly within the patient's vasculature, by means of introducer systems. These introducer systems typically include an elongated sheath which is inserted into the blood vessel or other portion of the patient's body, through which sheath the catheter or lead is introduced. In those circumstances in which the lead or catheter is to remain in the patient's body for a considerable period of time, it is desirable to be able to remove the introducer sheath without removing the lead or catheter.

One commonly employed mechanism for removing the introducer sheath from around the catheter or electrode lead is to provide the sheath with weakened zones on either side of the sheath, allowing it to be torn or split along weakened zones and removed from the catheter or lead. One introducer system employing this mechanism is illustrated in U.S. Pat. No. 5,409,469 issued to Schaerf, incorporated herein by reference in its entirety. Another commonly employed mechanism for removing the sheath from around the catheter or lead is to simply slit the sheath along its length as it is pulled proximally along the lead or catheter and out of the patient's body. One such slitter is disclosed in U.S. Pat. No. 4,997,424 issued to Little, also incorporated herein by reference in its entirety.

In many circumstances, it is desirable that a hemostasis valve be provided at the proximal end of the introducer sheath, allowing the introducer to be sealed around the lead or catheter body. The presence of the hemostasis valve, which typically includes a rigid housing containing a compressible seal which engages the circumference of the lead body, poses a problem with regard to removal of the introducer sheath. One approach to this problem is to make the hemostasis valve splittable, along with sheath. An introducer system employing this mechanism is disclosed in U.S. Pat. No. 5,125,904 issued to Lee, also incorporated herein by reference in its entirety. An alternative solution to the problem of providing a hemostasis valve in the context of a splittable sheath is to simply make the hemostasis valve removable from the sheath, so that the sheath thereafter can be split. Introducer systems employing this mechanism are disclosed in U.S. Pat. No. 5,250,033, issued to Evans et al and U.S. Pat. No. 4,473,067 issued to Schiff, both of which are also incorporated herein by reference in their entireties. In the Evans et al patent, a threaded coupling, provided with a pre-weakened zone, engages a removable hemostasis valve. In Schiff, a splittable sheath is simply compressed around the end of a removable hemostasis valve. In both cases, the proximal end of the sheath is not configured to be connectable to standard luer type fittings.

SUMMARY OF THE INVENTION

The present invention provides an introducer system having a slittable sheath in conjunction with a removable hemostasis valve. Unlike similar systems described above, the present sheath is provided with a luer hub on its proximal end, allowing interconnection both to the removable hemostasis valve and to other devices such as valves, T-fittings and the like, using the luer hub. In conjunction with development of the invention, the inventors have determined that provision of a weakened zone, rendering the luer hub splittable, also renders it mechanically less reliable than would be desired. In order to provide a reliable mechanical and fluid connection to the hemostasis valve, the present inventors have designed a luer hub specifically adapted to be slit using a conventional catheter slitter. The improved luer hub comprises a relatively thin walled, generally conical or cylindrical member provided with one or more laterally extending tabs for engagement with the internal threading of a luer fitting, such as the luer fitting on the associated hemostasis valve. The tab or tabs may be molded as part of the slittable conical or cylindrical member or may be located on a rib or ribs extending longitudinally along the conical or cylindrical member. At least one portion of the conical or cylindrical member, hereafter referred to as the "slittable portion" is intended to be slit by means of a slitter, after removal of the associated hemostasis valve. The slitter also is employed to slit the introducer sheath, carrying the luer hub. The slittable portion of the conical or cylindrical member is located angularly displaced from the tab or tabs. The luer hub is preferably also provided with a handle, coupled to the conical member and angularly displaced from the portion of the conical or cylindrical member which is intended to be slit. The handle is preferably located diametrically opposite the slittable portion of the conical member, and if a longitudinally extending rib is provided it is longitudinally aligned with the rib.

In a preferred embodiment of the invention, the sheath is reinforced by means of one or more reinforcement fibers or bands, which are preferably arranged as a coil or braid, along the length of the sheath body. In construction, the sheath in these embodiments thus resembles a guiding catheter, and provides for a high degree of kink resistance along the length of the sheath when bent. The sheath may also optionally be provided with a slittable radiopaque marker located at the distal tip of the sheath.

In one embodiment of the invention, the introducer system is provided with a slitter particularly optimized for use in conjunction with a reinforced introducer sheath. The slitter is provided with a groove, formed in the slitter handle in which the lead or catheter body is located, protecting it from damage by the cut edges of the sheath, as the sheath is pulled proximally over the slitter.

BRIEF DESCRIPTION OF THE DRAWINGS

FIG. 1 is a plan view of an introducer according to the present invention.

FIGS. 2, 3 and 4 illustrate various alternative embodiments of the sheath body 10.

DETAILED DESCRIPTION OF THE EMBODIMENT

Figure 5:
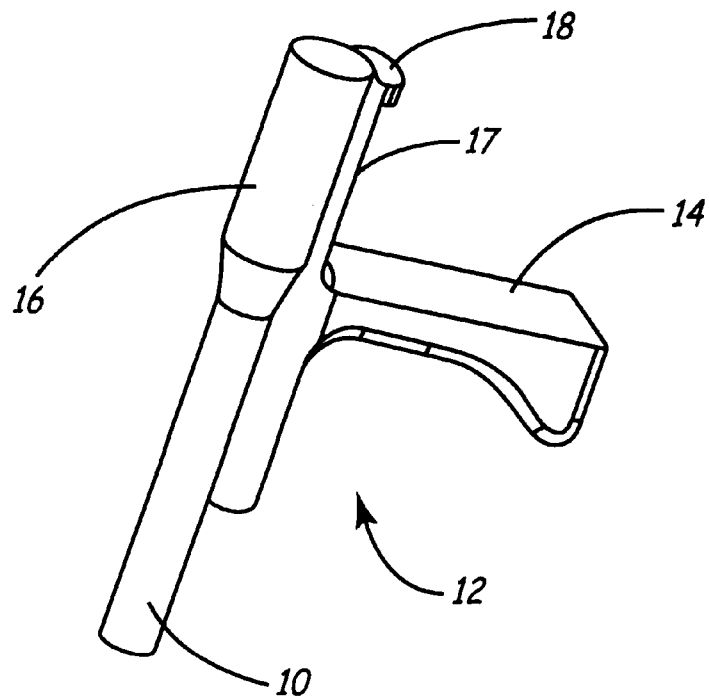
FIGS. 5 and 6 are perspective views of the luer hub and proximal portion of the introducer sheath illustrated in FIG. 1.

FIG. 1 is a plan view of an introducer according to the present invention. The introducer is provided with an elongated sheath body 10 which carries a slittable luer lock assembly 12, molded to its distal end. Luer lock assembly 12 may be fabricated of multiple components, or is more preferably molded as a single piece part, molded to the proximal end of the sheath body 10. Slittable luer hub 12 comprises a hollow, generally conical member 16 which carries an elongated rib 17, which in turn carries a laterally extending flange 18 which engages into the internal threading of a corresponding luer fitting, located in the hemostasis valve to be attached to the sheath. The slittable portion of conical member 16, comprising that portion angularly displaced from the rib 17, is thin enough that it may be readily split using a conventional slitter of the type employed in conjunction with lead introducers, for example, as disclosed in the Little patent cited above. The conical member 16 must also be sufficiently compliant that when slit, the cut edges may be spread far enough apart to permit passage of the introduced lead or catheter therebetween. Alternative embodiments of the invention may employ an additional rib or ribs, each carrying a flange, provided that there is sufficient space between the ribs to allow passage of a sheath slitter. The assembly is provided with a handle 14 which allows the physician to pull the sheath against the slitter, during removal of the sheath. At the distal end of the sheath is a radiopaque marker band 20 which may be formed of a slittable thin tube or ring of a radiopaque material molded into the distal end of the sheath body 10.

FIGS. 2, 3 and 4 illustrate various alternative embodiments of the sheath body 10. All three illustrated embodiments include an internal reinforcement including one or more spirally wound fibers, preferably taking the form of a mesh or braided tube, molded into the body of the sheath 10.

FIG. 2 illustrates a first embodiment of a sheath 10a employing reinforcements 22 which take the form of flat ribbons of reinforcing material, sandwiched between inner and outer tubular layers 24 and 26. The reinforcing fibers 22 are preferably made of a high strength polymer such as nylon, PET, or the like, and are wound in opposite directions to form a tubular mesh or braid. The inner and outer layers of the sheath body 26 and 24 may be fabricated of materials conventionally employed to manufacture guiding catheters, including polyamides, polyesters, polyether block amides, polyurethanes, PTFE, silicone rubbers, and the like.

FIG. 3 illustrates an alternative embodiment of a sheath 10b according to the present invention. In this case, the reinforcement takes the form of circular fibers 28 embedded between inner and outer layers 32 and 30, respectively of the catheter body.

FIG. 4 illustrates an embodiment in which the reinforcement fibers 36 are embedded in a monolithic sheath body 10c formed of a single material 34.

Appropriate mechanisms for fabrication of the sheath body are disclosed in U.S. Pat. No. 5,624,617 issued to Sorabella; U.S. Pat. No. 5,509,910 issued to Lunn; and U.S. Pat. No. 5,545,149 issued to Brin et al, all of which are incorporated herein by reference in their entireties. The thickness of the sheath, including its inner and outer two layers is a function of the specific materials chosen. However, in one particularly preferred embodiment, the sheath is manufactured having an outer layer of PEBAX® 70D to 35D polyether block amide manufactured by Atochem North America, Inc., Philadelphia, Pa., of approximately 0.006" in thickness, an inner layer, also of PEBAX® 70D to 35D polymer of approximately 0.004" in thickness and a braided reinforcement layer of 0.002" diameter 302 stainless steel wires, preferably quarter hard to half hard tempered, having an ultimate tensile strength of approximately 125,000–200,000 psi.

Figure 6:
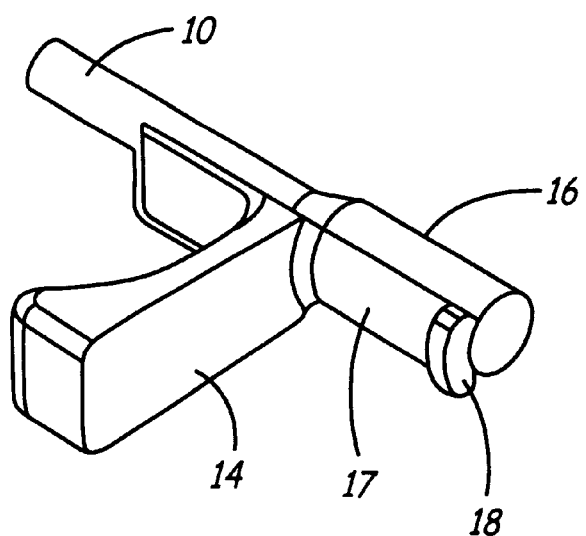

FIGS. 5 and 6 are perspective views of the proximal portion of the introducer sheath and slittable luer hub assembly illustrated in FIG. 1. In this view, it can be seen that the luer hub assembly 12 is formed as a single molded component, molded to the distal end of the sheath body 10. These drawings illustrate the configuration of the handle 14, the conical portion 16, the longitudinally extending rib 17 and the laterally extending flange 18. The longitudinally extending rib 17 extends over less than half of the circumference of the conical member 16 in the illustrated embodiment. However, in alternative embodiments, it might extend over a greater or lesser portion of the circumference of the conical member 16. The reinforcing rib 17 provides structural rigidity to the assembly and acts as a strain relief to sheath 10. The conical member 16, due to the fact that it is not manufactured with any pre-weakened zones, provides for substantial mechanical integrity when coupled to a standard luer fitting, even though it is provided with a relatively thin wall. The conical member is preferably molded of a polymer of 55D to 70D hardness and preferably is between 0.010" and 0.040" in thickness. For example, the luer hub assembly may be molded of PEBAX® 70D polymer and the wall of the conical member 16 may be 0.010" in thickness, in areas in which a reinforcing rib is absent, or may be molded of PEBAX® 55D polymer and the wall of the conical member 16 may be 0.040" in thickness, in areas in which a reinforcing rib is absent.

Figure 7:
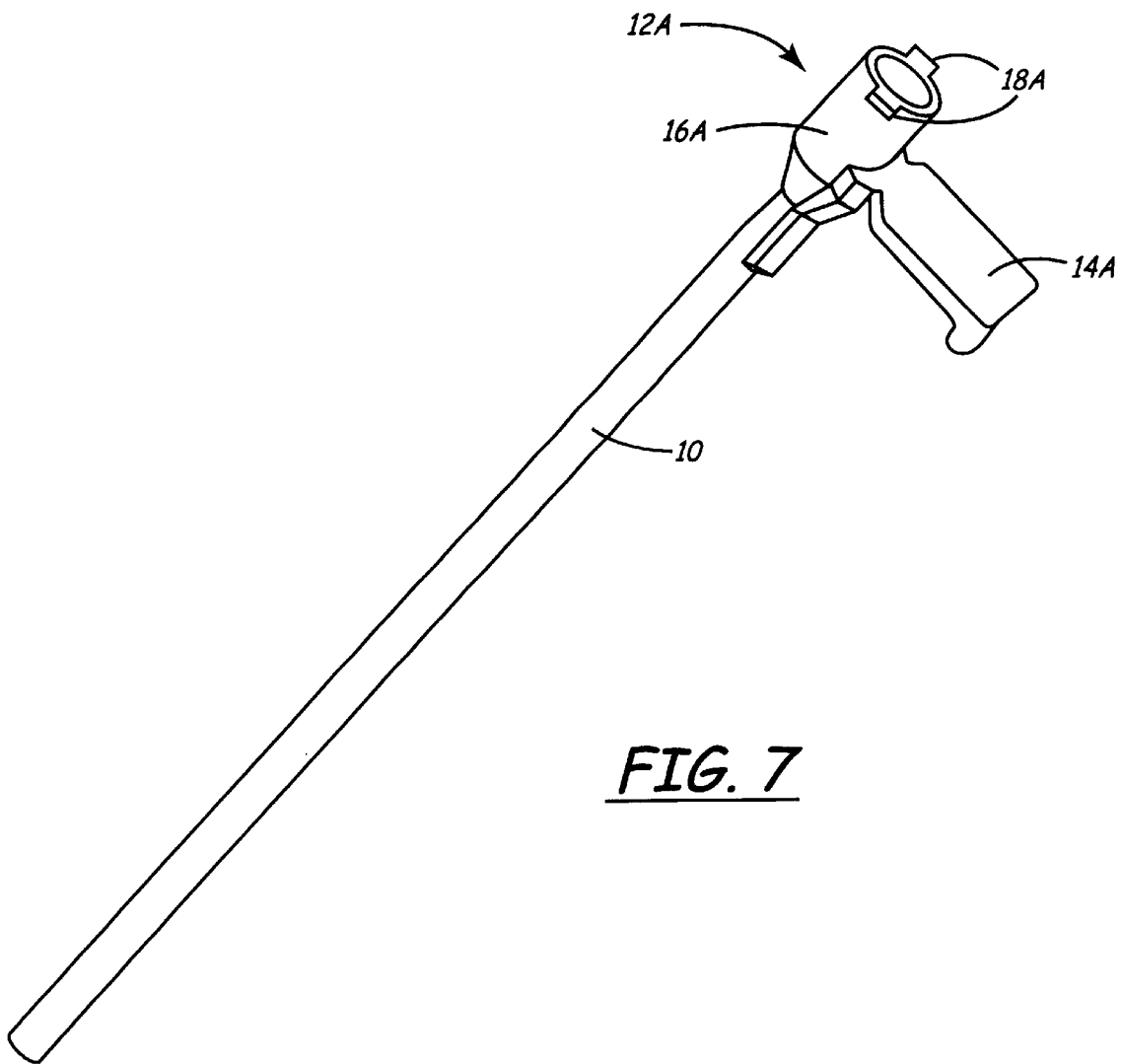
FIGS. 7, 8 and 9 are perspective views of the luer hub and proximal portion of an alternative embodiment of an introducer sheath according to the present invention.

FIG. 7 is a perspective view of sheath 10 with a first alternative embodiment of a slittable luer hub 12A attached. In this embodiment, cylindrical member 16A carries two tabs 18A which serve as threads to engage a female luer fitting and no longitudinal reinforcing rib is provided. The slittable portion of member 16A is located between the tabs 18A. A handle 14A is provided, located diametrically opposite the slittable portion of the conical member 16A.

Figure 8:
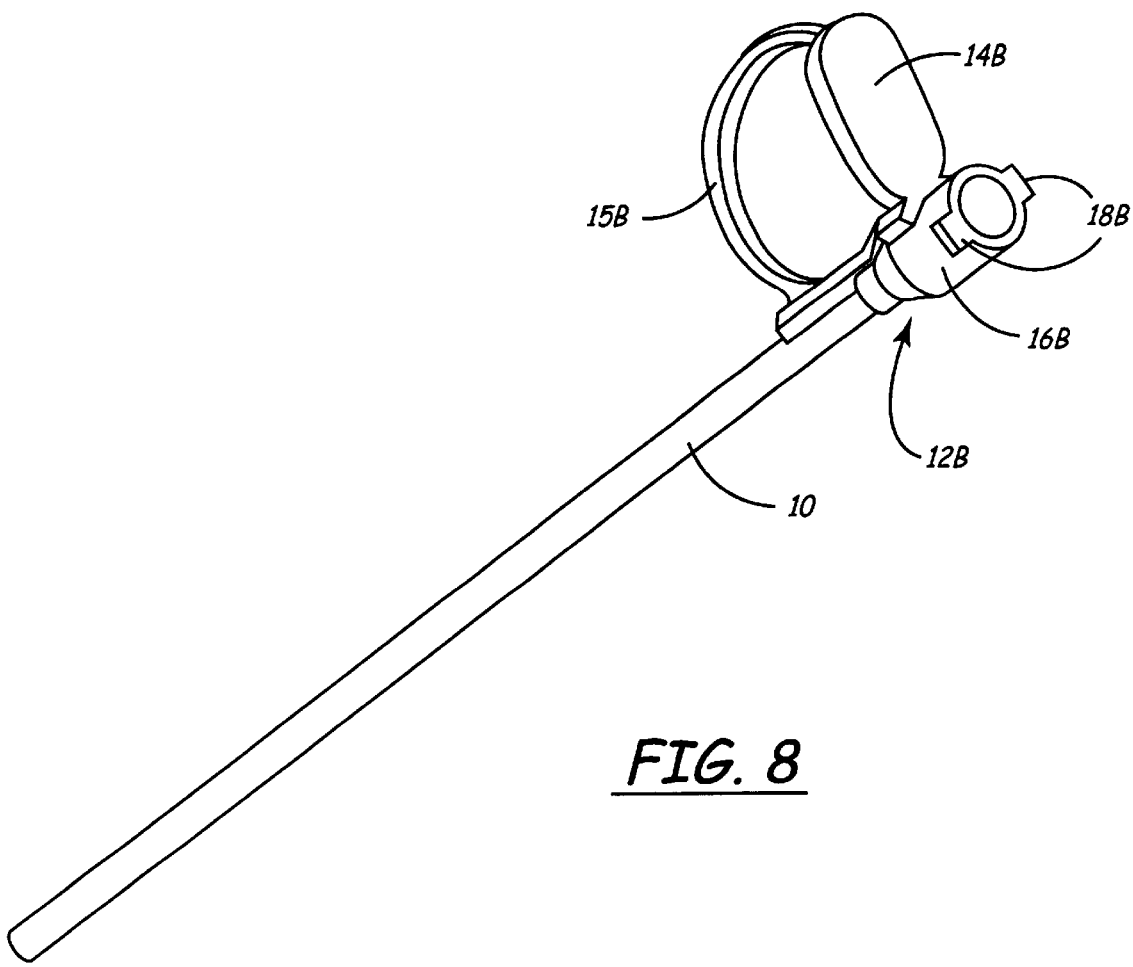

FIG. 8 is a perspective view of sheath 10 with a second alternative embodiment of a slittable luer hub 12B attached. In this embodiment, cylindrical member 16B also carries two tabs 18B which serve as threads to engage a female luer fitting and no longitudinal reinforcing rib is provided. The slittable portion of member 16B is located between the tabs 18B. A handle 14B is provided, located diametrically opposite the slittable portion of member 16B and includes a loop 15B to assist the physician in maintaining a grasp.

Figure 9:
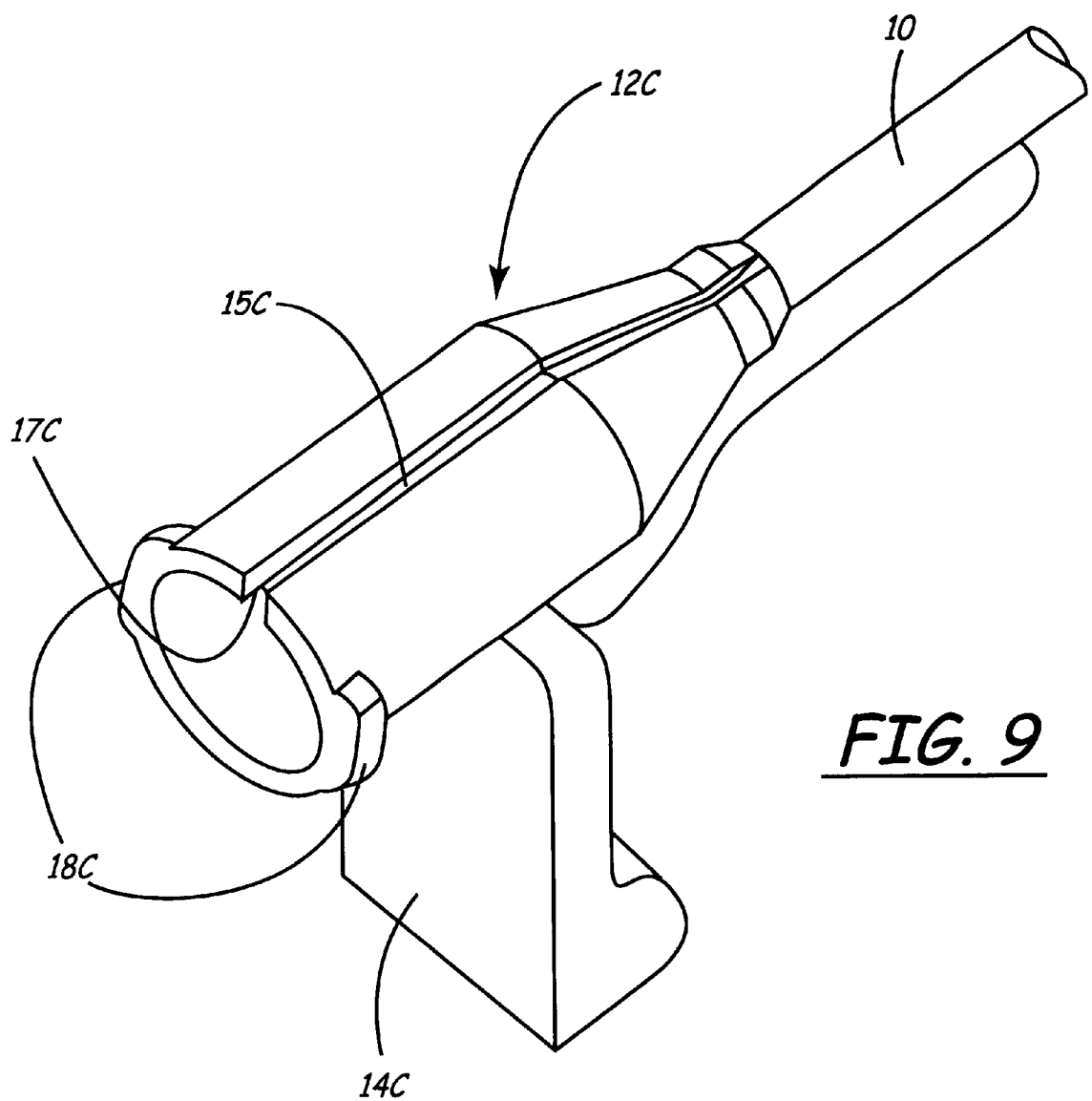

FIG. 9 is a perspective view of sheath 10 with a third alternative embodiment of a slittable luer hub 12C attached. In this embodiment, cylindrical member 16C also carries two tabs 18C which serve as threads to engage a female luer fitting and no longitudinal reinforcing rib is provided. The slittable portion of member 16C is located between the tabs 18C and is provided with a groove 15C an associated proximally facing notch 17C to guide the slitter during the slitting procedure. As illustrated in FIG. 8, a handle 14B is provided, located diametrically opposite the slittable portion of member 16B and optionally includes a loop 15B to assist the physician in maintaining a grasp.

Figure 10:
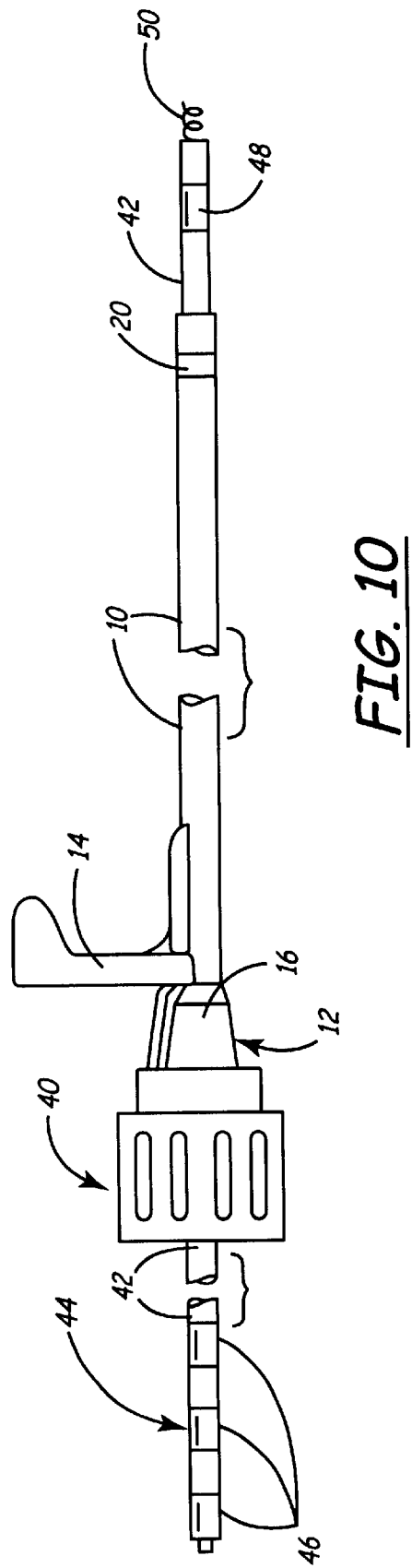
FIG. 10 shows the introducer and associated hemostasis valve, in conjunction with an implantable electrode lead.

FIG. 10 illustrates the introducer sheath of FIG. 1 in conjunction with a hemostasis valve 40 and an associated electrode lead, extending through the sheath 10. The lead is provided with an elongated insulative lead body 42 which carries an in-line connector assembly 44 at its proximal end, carrying electrical connector rings 46. The connector assembly 44 may correspond to that disclosed in U.S. Pat. No. 5,766,042 to Ries et al, and incorporated herein by reference in its entirety. Other conventional lead connectors may be substituted. At its distal end, the lead body 42 carries a ring electrode 48 and a helical electrode 50, each of which are coupled to one of the electrical connectors 46 located on the connector assembly 44.

In use, the sheath 10 is inserted into the vascular system and advanced to a desired location within the body. The lead 42 is then advanced out of the distal end of the sheath, allowing the helical electrode 50 to be screwed into body tissue. Hemostasis valve 40 is a conventional hemostasis valve provided with a luer fitting at its distal end, and which is mounted to the slittable luer hub 12. For example, a Tuohy-Borst model S1178014 valve with a male luer lock, manufactured by B. Braun, may be employed. Alternatively, hemostasis valves with Y-fittings or side ports may be substituted. Hemostasis valve 40 provides a fluid seal around the circumference of the lead body 42, preventing flow of blood or other fluids out of the introducer sheath. The hemostasis valve must be sized to permit the valve to seal to the lead body and must be able to dilate to permit passage of the connector assembly on the lead therethrough.

As illustrated, the introducer sheath has a generally straight configuration. However, the introducer sheath may alternatively have a pre-curved configuration, facilitating advancement of the distal end of the sheath to a desired location within the patient's body, for example, as disclosed in U.S. Pat. No. 5,571,161 issued to Starksen and incorporated herein by reference in its entirety, or may comprise the innermost sheath of a two sheath introducer system providing for variable curvature, for example as disclosed in U.S. Pat. No. 5,267,982 issued to Sylvanowicz, also incorporated herein by reference in its entirety. After electrode 50 is affixed to body tissue at desired location, the hemostasis valve 40 is unscrewed and moved proximally over the connector assembly 44 of the associated lead. The introducer sheath is then ready for removal from the lead body 42.

Figure 11:
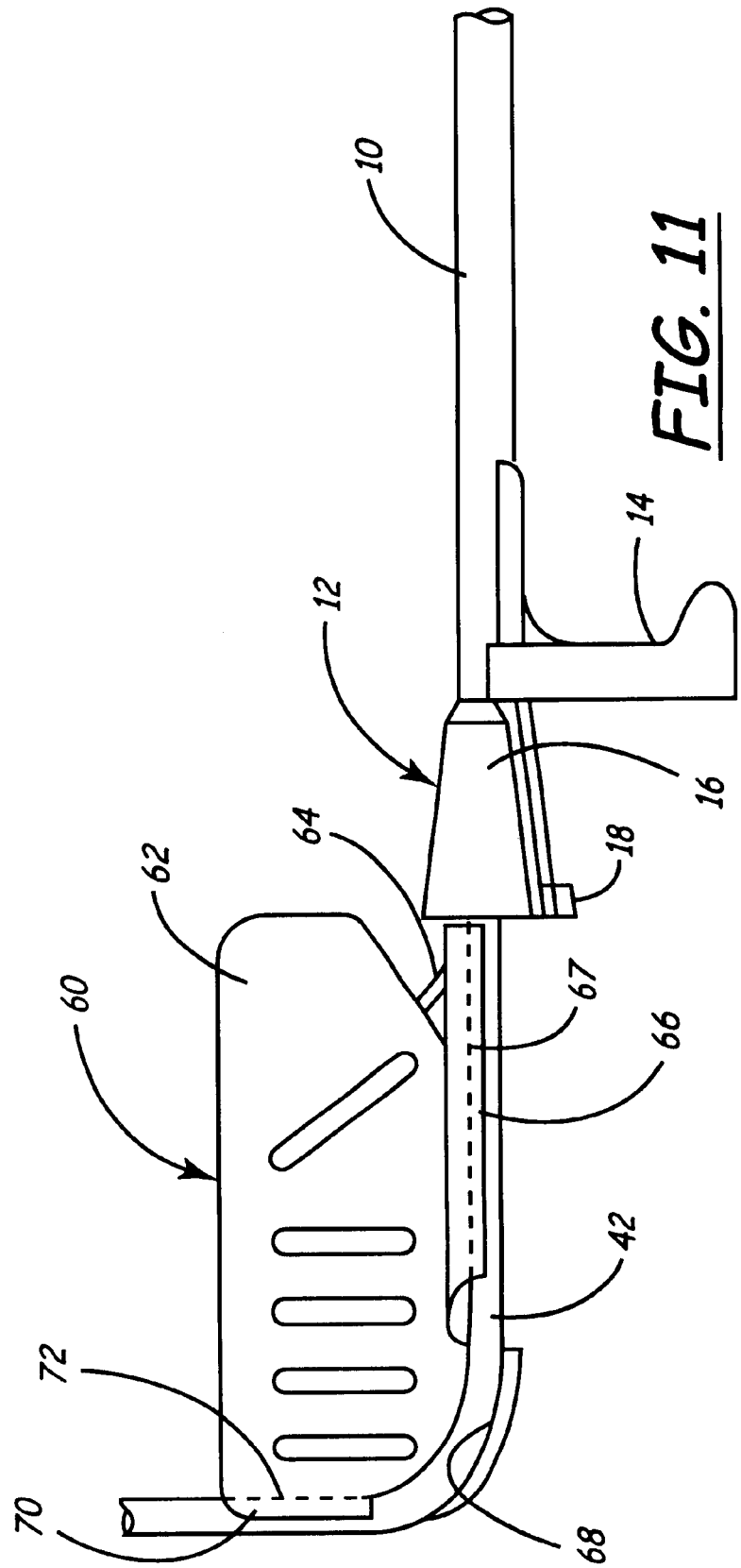
FIG. 11 shows the slitter mounted to the implantable lead, after removal of the hemostasis valve.

FIG. 11 illustrates the introducer sheath, ready for removal, in conjunction with an associated slitter 60, particularly optimized for use in conjunction with reinforced introducer sheaths. The slitter 60 is provided with a handle 62 which carries a blade 64, has two generally planar opposing main surfaces and circumferential edge surfaces and is provided with a C-shaped channel member 66 located along a lower edge surface of the handle, corresponding to that disclosed in the above cited Little '424 patent, the innermost extent of the C-shaped channel indicated by broken line 67. The C-shaped channel in member 66 engages the lead body 40 in the vicinity of the blade 64, preventing relative movement of the slitter and the lead body. In addition, the main surface of one side of the handle 62 is provided with a groove 68 for receiving the lead body 42 during slitting of the introducer sheath 10. Groove 68 serves to deflect the lead body relative to the slit sheath so that it exits the sheath laterally. The proximal end portion 70 of the handle 62 is also provided with a second C-shaped groove perpendicular to the first C-shaped groove, the innermost extent of the second C-shaped groove indicated by broken line 72. This second C-shaped groove engages lead body 42 proximal to groove 68 and assists in maintaining the lead body 42 in groove 68 during removal of the sheath. The groove 68 and the second C-shaped groove impart a curved configuration to the lead body 42 proximal to the blade 64, curving the lead body relative to the axis of the lead in the vicinity of the blade 64, which also assists in preventing the proximal portion of the lead from contacting the cut edges of the sheath. The thickness of the handle 62 in the vicinity of groove 68 is greater than the thickness of the lead body 42. As such, as the sheath is passed proximally along the slitter during removal from the lead body, the cut edges of the sheath 10, and in particular the cut ends of the internal reinforcement therein are spaced from the lead body in the region in which the lead body laterally exits the sheath, protecting the portion of the lead body 42 in groove 68 from damage. All other numbered components correspond to identically numbered components in FIGS. 1–6 and 10.

While the slitter 60 as illustrated employs a groove molded into the side or main surface of the handle to protect the lead body from damage from the cut edges of the sheath, equivalent alternatives may be substituted. For example, a groove may instead be molded extending inwardly from the edge of the handle proximal to the C-shaped member and configured to engage the lead body, curving it away from the slit sheath and protecting the lead body from the cut edges of the sheath. The specific mechanism employed to protect the lead body from damage thus need not precisely correspond to the illustrated embodiment, so long as it includes a mechanism to deflect the slit portion of the sheath and the lead body relative to one another to cause the lead body to laterally exit the slit sheath and a mechanism to prevent contact of the lead body with the sheath in the region in which the lead body exits laterally from the sheath.

Figure 12:
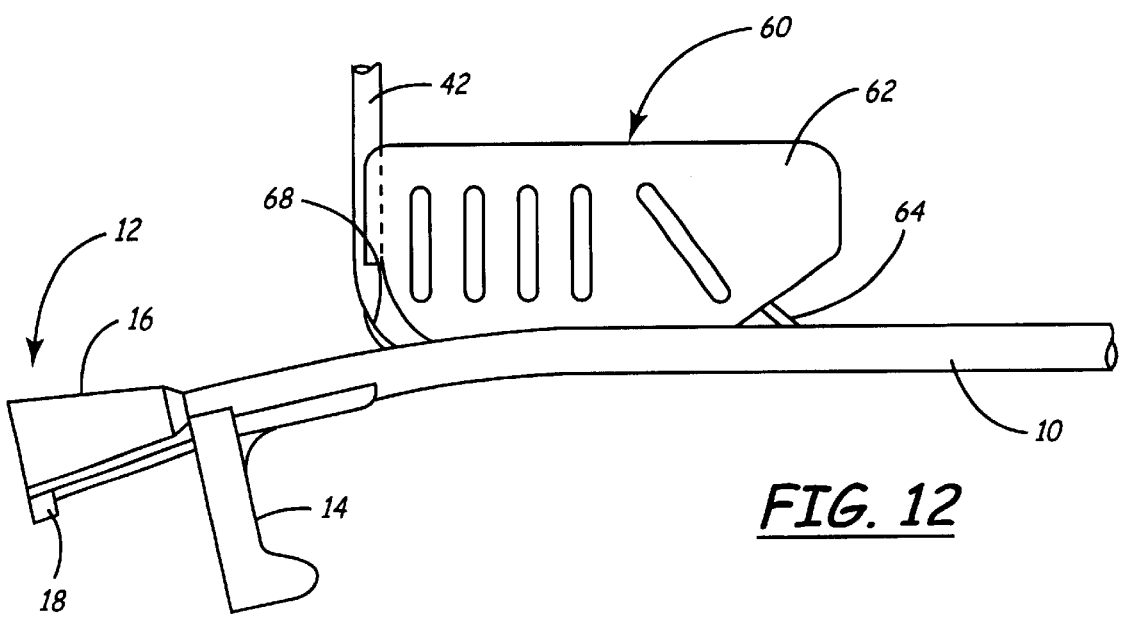
FIG. 12 shows the slitter as the introducer is pulled proximally over the slitter to remove it from the lead body.

FIG. 12 illustrates the sheath and slittable luer hub assembly 12 after being pulled proximally along the slitter 60. In this view, it can be seen that the thin walled, generally conical member 16 has already been slit by blade 64, along with a portion of the introducer body 10. The cut edges of the sheath pass along the handle 62 of the slitter, across groove 68, and are thus spaced from lead body 42, protecting it from damage. All other numbered components correspond to identically numbered components in FIGS. 1–6, 10 and 11.

Figure 13:
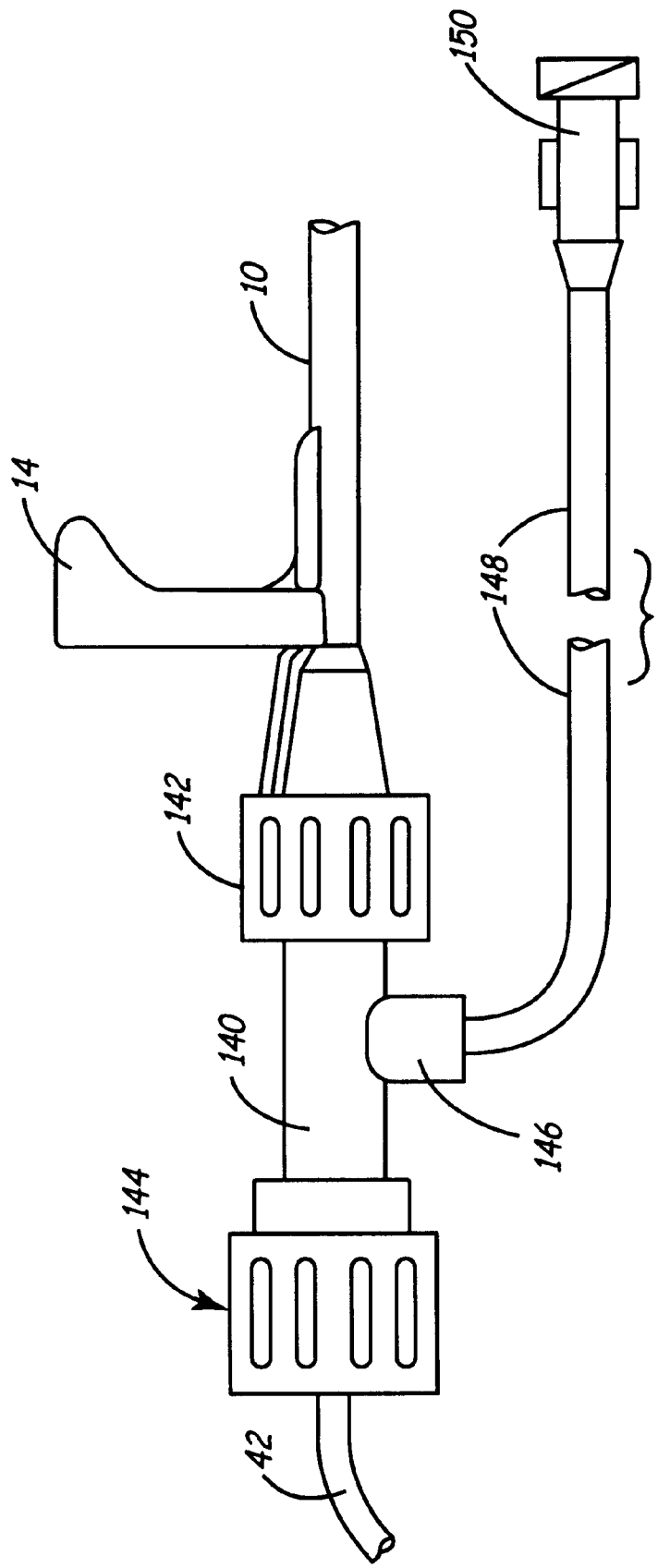
FIG. 13 shows the introducer of FIG. 1 in conjunction with an alternative hemostasis valve including a side port.

FIG. 13 is a plan view of the proximal portion of an alternative embodiment of the present invention, in which the removable hemostasis valve is provided with a side port to allow for irrigation during passing of the lead. The removable hemostasis valve may take the form of that disclosed in U.S. Pat. No. 5,669,881 issued to Dunshee, and incorporated herein by reference in its entirety. In this embodiment, the hemostasis valve 144 is mounted to a T-fitting 140 which carries a luer fitting 142 at its proximal end, which in turn engages the slittable luer hub 12. A side port 46 is provided, coupled to an elongated flexible tube 148 which in turn extends to a conventional rigid plastic luer lock 150 which may be coupled to a syringe or other fluid source, permitting irrigation around lead body 42, along the length of sheath body 10. The hemostasis valve 144 prevents leakage of the irrigation fluid from the proximal end of the fitting 140.

While the above embodiments all employ sheath bodies which are reinforced along their length, it is believed that the present invention is also valuable in the conjunction with lead introducer systems employing sheaths fabricated of simple extruded polymer tubes, for example as disclosed in the above cited Schaerf patent. The embodiments illustrated above should be considered exemplary, rather than limiting with regard to the claims which follow.

In conjunction with the above specification, we claim:
What is claimed is:

1. A method of introducing a lead or catheter into a patient's body, comprising:

introducing an introducer comprising an elongated introducer sheath, a luer hub, and a hemostasis valve removably mounted to the luer hub into a desired location of a patient's body;

advancing a lead or catheter through the hemostasis valve, luer hub and introducer sheath to a desired location in a patient's body;

removing the hemostasis valve from the introducer sheath; and slitting the luer hub and introducer sheath to remove it from the lead or catheter body.

2. The method of claim 1, wherein the step of slitting includes deflecting a portion of the lead or catheter relative to the slit sheath so that the deflected portion exits the sheath laterally.

3. The method of claim 2, wherein the step of slitting further includes preventing contact of the lead or catheter with the sheath in a region in which the lead or catheter exits laterally from the sheath.

4. The method of claim 1, further comprising the step of imparting a curved configuration to the lead or catheter proximal to a blade to curve the lead or catheter relative to an axis of the lead or catheter along the blade to prevent a proximal portion of the lead or catheter from contacting cut edges of the sheath.

5. The method of claim 1, wherein the step of slitting further comprises the step of passing the sheath proximally along a slitter so that cut edges of the sheath are spaced from the lead or catheter in a region in which the lead or catheter laterally exits the sheath.

* * * * *